United States Patent [19]

Periasamy

[11] Patent Number: 4,471,134

[45] Date of Patent: Sep. 11, 1984

[54] PREPARATION OF TRIMETHOXYBENZOATE ESTERS AND TRIMETHOXYBENZOIC ACID

[75] Inventor: Muthunadar P. Periasamy, Creve Coeur, Mo.

[73] Assignee: Mallinckrodt, Inc., St. Louis, Mo.

[21] Appl. No.: 426,450

[22] Filed: Sep. 29, 1982

[51] Int. Cl.³ ............................................. C07L 69/76
[52] U.S. Cl. ...................................... 560/64; 560/68; 562/473; 562/475
[58] Field of Search .................... 560/64, 68; 562/473, 562/475

[56] References Cited

FOREIGN PATENT DOCUMENTS 123938 9/1981 Japan .

OTHER PUBLICATIONS

Kutani Noboru, Chem. Pharm. Bull., vol. 8, pp. 72–76, (1960).
Britton, et al., J. Chem. Soc., (1966), pp. 783–790.
Kirk–Othmer, Encyclopedia of Chem. Technology, vol. 7, 1951, pp. 45–53.

*Primary Examiner*—Paul J. Killos
*Attorney, Agent, or Firm*—Richard G. Jackson; Roy J. Klostermann; Lynden N. Goodwin

[57] ABSTRACT

A mixture of intermediate products including a carboxylic salt of 3,4,5-trimethoxybenzoic acid (TMB acid) and a dimethoxy benzoic acid derivative of such salt further containing an oxygen anion in the 3,4, or 5 position is prepared by initially reacting hydrolyzable tannin with a methylation agent in an alkaline medium under methylation conditions to form methylated tannin and thereafter hydrolyzing the methylated tannin by reaction thereof with a hydrolysis agent under alkaline hydrolysis conditions. The resulting reaction mixture is then methylated to form a reaction mixture containing methyl 3,4,5-trimethoxybenzoate and a salt of 3,4,5-trimethoxybenzoic acid. TMB acid can be formed in high yield by conversion of both the methyl ester thereof and the salt thereof. Such conversion can be effected by hydrolyzing the reaction mixture followed by acidification thereof.

11 Claims, No Drawings

PREPARATION OF TRIMETHOXYBENZOATE ESTERS AND TRIMETHOXYBENZOIC ACID

BACKGROUND OF THE INVENTION

This invention relates to a process for preparing methyl 3,4,5-trimethoxybenzoate from hydrolyzable tannin and to a process for preparing 3,4,5-trimethoxybenzoic acid via preparation of such methyl ester.

3,4,5-Trimethoxybenzoic acid (hereinafter sometime referred to as "TMB-acid") is useful for preparing pharmaceutical compositions, e.g., trimethoprim. Heretofore, TMB-acid has been prepared by a multiplicity of steps including (1) hydrolyzing tannin or a tannin-containing material to form gallic acid; (2) isolating the gallic acid; (3) methylating the isolated gallic acid to form a mixture of TMB-acid and its methyl ester; (4) saponifying the acid-ester mixture; (5) acidifying the saponified mixture to liberate TMB-acid from its salt; and (6) recovering the TMB-acid. Steps (1) and (2) involving tannin hydrolysis and gallic acid isolation are described in Krueger et al., U.S. Pat. No. 2,732,992. Japanese Pat. No. 56-123938 indicates that methylation of gallic acid and one or more of the remaining steps are described in Org. Syn. Coll., Vol. I, 537, Corriere Favm., 22, 196 (1967). The foregoing highly multiple step process suffers a number of drawbacks, including need for isolation of gallic acid, high cost, and long reaction time where the tannin is hydrolyzed to gallic acid under acid hydrolysis conditions and decomposition of gallic acid to pyrogallic acid where such tannin hydrolysis is effected under alkaline conditions. Accordingly, there is a substantial need in the art for improved processes for preparing TMB-acid and related TMB compounds.

It has now been found that TMB-acid and the methyl ester thereof can be formed by an improved process which obviates the need for hydrolyzing tannin to gallic acid and isolating intermediates.

DESCRIPTION OF THE INVENTION

Generally stated, the present invention provides a process for preparing the methyl ester of 3,4,5-trimethoxybenzoic acid, which comprises:

(a) reacting hydrolyzable tannin with a methylation agent in an alkaline medium under methylation conditions to form methylated tannin, (b) hydrolyzing the methylated tannin by reaction thereof with a hydrolysis agent under alkaline hydrolysis conditions to form a mixture of intermediates comprising a 3,4,5-trimethoxybenzoate salt of the hydrolysis agent and a dimethoxybenzoic acid derivative of such salt, the derivative containing an oxygen anion in the 3,4 or 5 position, (c) methylating said intemediates to form a reaction mixture comprising methyl 3,4,5-trimethoxybenzoate and a carboxylic salt of 3,4,5-trimethoxybenzoic acid (TMB acid), and (d) recovering the methyl 3,4,5-trimethoxybenzoate ester.

This invention also provides a process for preparing 3,4,5-trimethoxybenzoic acid (TMB acid) which comprises carrying out the above steps (a), (b) and (c) in that order, and thereafter:

(d) saponifying the reaction mixture from step (c) to convert the methyl 3,4,5-trimethoxybenzoate ester to carboxylic salt of TMB acid, and (e) acidifying the resulting saponified reaction mixture to convert the salt to TMB acid.

DETAILED DESCRIPTION OF THE INVENTION

In the first step of the process, hydrolyzable tannin is reacted with a methylation agent in an alkaline medium under methylation conditions to form methylated tannin. The tannin or tannic acid employed can be any hydrolyzable tannin such as that obtained by extraction thereof from such tannin-containing materials as tara pods, Chinese nut galls, Aleppo galls, sumac leaves, etc. Taratannin (i.e., tannin obtained by extraction from tara pods) is preferred. Methods for extracting tannin from tannin-containing materials are well known in the art.

Any suitable methylation agent can be used. Suitable methylation agents include, for example, dimethyl sulfate, methyl p-toluene sulfonate, methyl iodide, diazomethane etc. Dimethyl sulfate is preferred.

Any suitable alkaline medium can be employed for the methylation reaction. The alkaline medium includes a liquid solvent or dispersant such as water, ethyl acetate, methyl isobutyl ketone, acetone, etc. and an alkaline agent such as sodium hydroxide, potassium hydroxide, calcium hydroxide, ammonium hydroxide, organic amines (e.g., triethylamine), etc. Aqueous sodium hydroxide is preferred for the alkaline medium.

The methylation reaction is effected, for example, by initially forming a reaction mixture of the tannin, methylation agent (e.g., dimethyl sulfate), alkaline agent or base (e.g., sodium hydroxide), and the liquid solvent or dispersant (e.g., water). The methylation reaction may then be effected under any suitable methylation conditions, including for example heating with agitation at a temperature of about 15° to about 80° C. for a period of about 2 to about 8 hours.

The methylation agent is preferably employed in an amount at least equal to the stoichiometric amount required for conversion of all the hydroxyl groups of the tannin to methoxy groups. More preferably, a stoichiometric excess of the methylation agent is employed. The alkaline agent must be included in a sufficient amount such that the reaction mixture is above 7 pH, preferably at least 8 pH and more preferably at least 10 pH.

Where the tannin is taratannin and the methylation agent is dimethyl sulfate, the amount of dimethyl sulfate may be from 1.25 to about 2.75 parts by weight per one part by weight of taratannin. Corresponding molar ratios of other methylation agents can be employed for methylation of taratannin or other tannins. The amount of sodium hydroxide may be from about 0.75 to about 1.75 parts by weight of NaOH per one part by weight of taratannin. Corresponding molar ratios of other alkaline agents can be employed for taratannin or other tannins. As a general preference the base is employed as a 50% aqueous solution. Thus, for example, from about 1.5 to about 3.5 parts by weight of 50% aqueous sodium hydroxide may be employed per one part by weight of taratannin.

Any suitable concentration of tannin may be employed in the reaction mixture. Advantageously, the concentration of tannin is from about 0.5 to about 10 lbs. of tannin per gallon of solvent, preferably from about 2 to about 8 lbs./gal., and more preferably from about 3 to about 6 lbs./gal.

All the methylation agent and the alkaline agent can be added initially and simultaneously or in any sequence. Alternatively, these agents can be added incrementally with heating and agitation of the reaction mixture.

In a preferred embodiment, the methylation agent and alkaline agent are added simultaneously and incrementally over a period of from about 3 to about 6 hours at a reaction temperature of from about 20° to about 50° C. (Optionally, the reaction mixture can be agitated for an additional period, e.g., from about 2 to about 6 hours, at a reaction temperature of about 20° to about 50° or 60° C. to aid in maximizing the extent of methylation).

With or without such additional agitation, hydrolysis of the resulting methylated tannin is thereafter effected by heating with agitation under hydrolysis conditions, e.g., maintenance of a reaction temperature of about 60° to about 110° C. for about 0.5 to about 6 hours. Heating with agitation can be effected advantageously by refluxing the reaction mixture. Preferred hydrolysis conditions include maintenance of a reaction temperature of about 80° to about 105° C. for about 1 hour to about 4 hours. (Optionally, at this stage, the reaction mixture is cooled and any precipitated side products are removed by filtration, centrifuging or the like.)

The above-described hydrolysis involves reaction of the methylated tannin with a hydrolysis agent under alkaline hydrolysis conditions to form a salt of TMB acid and the hydrolysis agent. Suitable hydrolysis agents include, for example, sodium hydroxide, potassium hydroxide, calcium hydroxide, ammonium hydroxide, organic amines (e.g., triethylamine), etc. The same material can serve as both the alkaline agent in the methylation step and as the hydrolysis agent in the hydrolysis step. Sodium hydroxide is preferred for use as both the alkaline agent and the hydrolysis agent. The amount of sodium hydroxide required for hydrolysis may be added to the reaction mixture prior to, during, or after the methylation reaction.

The above given amounts of sodium hydroxide generally will suffice to serve both the alkaline agent and hydrolysis agent functions. If desired an additional amount of sodium hydroxide or other hydrolysis agent may be added after methylation to aid in maximixing hydrolysis of the methylated tannin.

Advantageously, hydrolysis of the methylated tannin can be effected without isolation thereof from the reaction mixture.

Preferably, both the methylation step and the hydrolysis step are carried out under an inert atmosphere, preferably nitrogen, and in the presence of an oxygen scavenger, preferably sodium bisulfite.

After completion of the hydrolysis, the reaction mixture contains not only monovalent anions of the formula

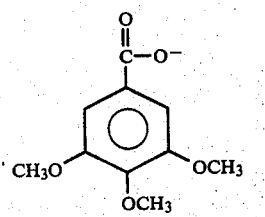

(Formula I)

but also contains divalent anions of the formula

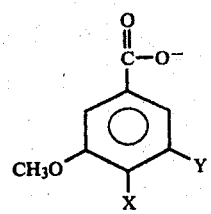

(Formula II)

where X is a methoxy (CH₃O—) group or an oxygen ion (O⁻) and Y is a methoxy group or an oxygen ion subject to the provisos that X is methoxy where Y is an oxygen ion and X is an oxygen ion where Y is methoxy. Associated with the monovalent anions of Formula I and with the divalent anions of Formula II are valence-satisfying amounts of cations (e.g., Na⁺) of the hydrolysis agent and/or alkaline agent employed. In general, X is a methoxy group and Y is an oxygen ion. Mixtures of anions within Formula II may be present, i.e., such anions wherein X is methoxy and such anions where Y is methoxy may both be present.

In the next step, the hydrolyzed reaction mixture is methylated by reaction with a methylation agent in an alkaline medium under methylation conditions. Unless otherwise noted, this step (the second methylation step of the process) can be carried out in accordance with the description set forth above for the initial step of methylating tannin. More particularly, this includes (but is not limited to) the above-described tannin methylation conditions (including temperatures, reaction times, etc.), methylation agent, and alkaline agent.

In the second methylation, dimethyl sulfate is the preferred methylation agent and sodium hydroxide is the preferred alkaline agent.

The methylation agent should be added in an amount sufficient to convert all the oxygen ions represented by X and Y in Formula II to methoxy groups. Since the anions of Formula I compete with the anions of Formula II for methyl groups from the methylation agent, the amount of methylation agent used should be in excess of the stoichiometric amount for converting the oxygen ions X and/or Y to methoxy groups. Where, for example, the methylation agent is dimethyl sulfate, from about 0.3 to about 1.5 parts of dimethyl sulfate may be used per one part of taratannin being converted. A sufficient amount of alkaline agent should be present during the second methylation to maintain the pH of the reaction mixture above 7 pH, preferably at least 8 pH and more preferably at least 10 pH. In general, addition of from about 0.25 to about 1.0 part of sodium hydroxide (about 0.5 to about 2.0 parts of 50% aqueous sodium hydroxide) is suitable for the second methylation. The methylation agent and alkaline agent may be added over a period of, for example, 0.5 to about 5 hours.

The preferences for use of nitrogen (or other insert atmosphere) and for use of sodium bisulfite (or other oxygen scavenger) apply also to the second methylation, which advantageously can be carried out in situ without need for isolation of intermediate products resulting from the hydrolysis step.

In a preferred embodiment, for the second methylation, the dimethyl sulfate (or other methylation agent) and the sodium hydroxide (or other alkaline agent) are added incrementally and simultaneously over a period of from about 1 to about 3 hours at a reaction temperature of from about 25° to about 45° C. Optionally, the reaction mixture can be agitated for an additional period, e.g., from about 1 to about 3 hours, at a reaction temperature of about 50° to about 65° C. to aid in maximizing the extent of the second methylation.

After completion of the second methylation, the reaction mixture includes a mixture of the methyl ester of TMB acid, i.e., methyl 3,4,5-trimethoxybenzoate, and the alkaline agent carboxylic salt of TMB acid (e.g., sodium 3,4,5-trimethoxybenzoate where sodium hydroxide is the alkaline agent). The same compound, e.g., sodium hydroxide, is preferably employed as the alkaline agent in both methylation steps and as the hydrolysis agent.

If desired, the methyl ester of TMB acid can be recovered after the second methylation using any suitable recovery procedure, e.g., extraction with a hydrocarbon solvent (e.g., hexane, etc.), centrifuging or filtration.

Instead of recovering the methyl ester after completion of the second methylation, TMB acid can be formed in high yield by conversion thereto of both the ester and the carboxylic salt. Such conversion is effected by saponifying or hydrolyzing the reaction mixture, thereby converting the methyl ester of TMB acid to carboxylic salt of TMB acid, and thereafter acidifying the saponified mixture to convert up to substantially all the carboxylate salt of TMB acid contained therein to TMB acid. The saponification step (the second hydrolysis step of the process) can be carried out in accordance with the description set forth above for the initial hydrolysis step. For example, the second hydrolysis includes reaction with a hydrolysis agent under preferably alkaline hydrolysis conditions. The second hydrolysis can be effected using the preceding hydrolysis conditions (including temperatures, reaction times, etc.), hydrolysis agent and amounts thereof. Sodium hydroxide is the preferred hydrolysis agent for the second hydrolysis. The hydrolysis agent for the second hydrolysis is added in an amount sufficient for conversion of at least substantially all the methyl ester of TMB acid to carboxylic salt of TMB acid. The required amount of hydrolysis agent can be added prior to, during or after the second methylation step. Preferred conditions for the second hydrolysis are maintenance of a reaction temperature of about 80° to about 105° C. for about 1 hour to about 4 hours.

After completion of the saponification, TMB acid can be formed by neutralizing the carboxylic salt of TMB acid in the reaction mixture by acidifying with any suitable acid. Preferably, the reaction mixture is cooled, e.g., to about 15° to about 45° C., prior to neutralization. Suitable acids include, for example, hydrochloric acid, sulfuric acid, phosphoric acid, etc. The acid employed is admixed with the reaction mixture, preferably by slowly adding the acid to the reaction mixture. The acid is added in an amount sufficient to acidify the mixture to a pH in the acid range, desirably from about 1 pH to about 6 pH, and preferably from about 3 pH to about 5 pH. Hydrochloric acid is preferred as the neutralizing agent. The acid may be employed as an aqueous solution or in the form of a solution thereof in an organic solvent, e.g., methanol, chloroform, etc.

Practice of the present invention is illustrated by the following non-limiting examples. All parts and percentages given throughout this disclosure, including the claims which follow, are by weight unless otherwise indicated.

EXAMPLE 1

Conversion of Taratannin to a Mixture of Methyl 3,4,5-Trimethoxybenzoate and 3,4,5-Trimethoxybenzoic Acid To 250 ml of aqueous taratannin (gallic acid content 97 grams, 0.57 mole) are added 183 gr of 50% NaOH and 228 grams of dimethyl sulfate in portions at 20°–40° C. over a 3–6 hour period. The reaction mixture is refluxed for 1–3 hours with 46 grams of 50% NaOH. Upon cooling to 30°–60° C., 37 gr of 50% NaOH and 114 grams of dimethyl sulfate are added in portions over a 2–4 hour period. After maintaining the reaction mixture at 50°–70° C. for 2–4 hours, the reaction mixture is cooled to yield 70–79 grams of methyl 3,4,5-trimethoxy benzoate in 54–61% yield. To the mother liquor sufficient amount of concentrated hydrochloric acid is added to precipitate and isolate 35–42 grams of dried 3,4,5-trimethoxybenzoic acid in 29–39% yield.

EXAMPLE 2

Conversion of Taratannin to a Mixture of Methyl 3,4,5-Trimethoxybenzoate and 3,4,5-Trimethoxybenzoic Acid To a 50 gallon reactor containing 120 lbs of aqueous taratannin (gallic acid content approximately 38 lbs), charge 72 lbs of 50% NaOH and 90 lbs of dimethyl sulfate in portions over a 2–6 hour period while maintaining a temperature of 20°–40° C. Then, the reaction mixture is refluxed for 2–4 hours with 23 lbs of 50% NaOH. Then, the reaction mixture is treated with 45 lbs of dimethyl sulfate and 13 lbs of 50% NaOH over a 2–4 hour period. After maintaining the reaction mixture at 50°–70° C. for 2–4 hours, the reaction mixture is cooled to yield 29–31 lbs of methyl 3,4,5-trimethoxybenzoate in 57–61% yield. The mother liquor is then acidified with concentrate HCl solution and 3,4,5-trimethoxybenzoic acid is isolated to give a dried yield of 38–40% (18–19 lbs).

EXAMPLE 3

Preparation of 3,4,5-Trimethoxybenzoic Acid from Aqueous Taratannin

To 250 ml of aqueous taratannin (Gallic acid content approximately 102 grams, 0.6 mole) are added 192 grams of 50% NaOH and 240 grams of dimethyl sulfate in portions at 20°–40° C. over a 3–6 hour period. The reaction mixture is refluxed for 1–3 hours with 48 grams of 50% NaOH. Upon cooling to 30°–60° C., 48 grams of 50% NaOH and 120 grams of dimethyl sulfate are added in portions over a 2–4 hour period. After treating with an additional 48 grams of 50% NaOH, the reaction mixture is refluxed for 1–3 hours. At the end of hydrolysis, the reaction mixture is cooled and acidified with concentrated hydrochloric acid to precipitate 3,4,5-trimethoxybenzoic acid (TMB acid). The precipitated product is isolated and dried to give 107–112 grams of TMB acid in 84–87% yield.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit and scope of the present invention.

What is claimed is:

1. A process for preparing the methyl ester of 3,4,5-trimethoxybenzoic acid, which comprises:
   (a) reacting hydrolyzable tannin obtained from a tannin-containing material selected from the group consisting of tara pods, Chinese nut galls, Aleppo galls and sumac leaves with a methylation agent in an alkaline medium under methylation conditions to form methylated tannin,
   (b) hydrolyzing the methylated tannin by reaction thereof with a hydrolysis agent under alkaline hydrolysis conditions to form a mixture of intermediates comprising a 3,4,5-trimethoxybenzoate salt of the hydrolysis agent and a dimethoxybenzoic acid derivative of such salt, the derivative containing an oxygen anion in the 3,4 or 5 position,
   (c) methylating said intermediates to form a reaction mixture comprising methyl 3,4,5-trimethoxybenzoate and a carboxylic salt of 3,4,5-trimethoxybenzoic acid (TMB acid), and
   (d) recovering the methyl 3,4,5-trimethoxybenzoate ester.

2. A process for preparing 3,4,5-trimethoxybenzoic acid (TMB acid) which comprises carrying out the following steps (a), (b) and (c) in that order:
   (a) reacting hydrolyzable tannin obtained from a tannin-containing material selected from the group consisting of tara pods, Chinese nut galls, Aleppo galls and sumac leaves with a methylation agent in an alkaline medium under methylation conditions to form methylated tannin,
   (b) hydrolyzing the methylated tannin by reaction thereof with a hydrolysis agent under alkaline hydrolysis conditions to form a mixture of intermediates comprising a 3,4,5-trimethoxybenzoate salt of the hydrolysis agent and a dimethoxybenzoic acid derivative of such salt, the derivative containing an oxygen anion in the 3,4 or 5 position,
   (c) methylating said intermediates to form a reaction mixture comprising methyl 3,4,5-trimethoxybenzoate and a carboxylic salt of 3,4,5-trimethoxybenzoic acid (TMB acid),
and thereafter
   (d) saponifying the reaction mixture from step (c) to convert the methyl 3,4,5-trimethoxybenzoate ester to carboxylic salt of TMB acid, and
   (e) acidifying the resulting saponified reaction mixture to convert the salt to TMB acid.

3. The process of claim 1 or 2 wherein said methylation agent is dimethyl sulfate, methyl p-toluene sulfonate, methyl iodide or diazomethane.

4. The process of claim 1 or 2 wherein said alkaline medium includes an alkaline agent selected from the group consisting of sodium, potassium, ammonium hydroxide and trimethylamine.

5. The process of claim 1 or 2 wherein said hydrolysis agent is selected from the group consisting of sodium, potassium, ammonium, and calcium hydroxide and triethylamine.

6. The process of claim 1 or 2 wherein said hydrolysis is effected in situ without isolation of said methylated tannin.

7. The process of claim 1 or 2 wherein said tannin is taratannin.

8. The process of claim 1 or 2 wherein at least a portion of the hydrolysis agent employed in step (b) is present in step (a) as an alkaline agent of the alkaline medium thereof, said alkaline agent being included in said medium in an amount such that the mole ratio of said alkaline agent to said tannin is a mole ratio corresponding to about 0.75 to about 1.75 parts by weight of sodium hydroxide per 1 part by weight of taratannin.

9. The process of claim 1 or 2 wherein said methylation is carried out at a temperature of from about 20° to about 60° C. and said hydrolysis step is carried out at a temperature of from about 60° to about 110° C.

10. The process of claim 1 or 2 wherein the methylated tannin formed in step (a) is hydrolyzed in step (b) without separation of the methylated tannin into components.

11. The process of claim 1 or 2 wherein said methylation agent is employed in step (a) in an amount such that the mole ratio of said methylation agent to said tannin is a mole ratio corresponding to about 1.25 to about 2.75 parts by weight of dimethyl sulfate per 1 part by weight of taratannin, and methylation is effected in step (c) employing a methylation agent in an amount such that the mole ratio of methylation agent employed in step (c) to the amount of tannin initially employed in step (a) is a mole ratio corresponding to about 0.3 to about 1.5 parts by weight of dimethyl sulfate per 1 part by weight of taratannin.

* * * * *